US00PP18059P2

(12) United States Plant Patent
Pieters

(10) Patent No.: US PP18,059 P2
(45) Date of Patent: Sep. 18, 2007

(54) ***CHRYSANTHEMUM* PLANT NAMED 'PPP PIZ R05'**

(50) Latin Name: *Chrysanthemum morifolium*
Varietal Denomination: PPP PIZ R05

(75) Inventor: Dirk Pieters, Oostnieuwkerke (BE)

(73) Assignee: Pieters Plant Production, Oostnieuwkerke (BE)

( * ) Notice: Subject to any disclaimer, the term of this patent is extended or adjusted under 35 U.S.C. 154(b) by 0 days.

(21) Appl. No.: 11/414,883

(22) Filed: Apr. 29, 2006

(51) Int. Cl.
*A01H 5/00* (2006.01)

(52) U.S. Cl. ..... Plt./293

(58) Field of Classification Search ..... Plt./293, Plt./287, 290
See application file for complete search history.

*Primary Examiner*—Kent Bell
*Assistant Examiner*—June Hwu

(57) ABSTRACT

A new and distinct *Chrysanthemum* plant cultivar is disclosed, characterized by large decorative type inflorescences, consistent flowering response to short days, blooming consistently after 49 days of short day length, bronze red ray florets, free branching habit, and a consistent natural season flowering habit during the first week of September.

1 Drawing Sheet

Latin name of the genus and species: *Chrysanthemum morifolium.*
Variety denomination: 'PPP PIZ R05'.

BACKGROUND OF THE INVENTION

The new cultivar 'PPP PIZ R05' is a product of a cross between the female parent 'GEDI TWO CAM' (U.S. Plant Pat. No. 14,472) and the male parent 'GEDI ONE SAV' (U.S. Plant Pat. No. 13,928). The new cultivar was discovered and selected by Dirk Pieters in September 2003 in Oostnieuwkerke, Belgium.

Asexual reproduction of the new cultivar 'PPP PIZ R05' by terminal cuttings and tissue culture was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP PIZ R05' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP PIZ R05.' These characteristics in combination distinguish 'PPP PIZ R05' as a new and distinct *Chrysanthemum* cultivar:

1. Red bronze inflorescences;
2. Consistent flowering response to short days, blooming consistently after 49 days of short day length;
3. Free branching habit; and
4. Consistent natural season flowering habit during the first week of September.

Plants of the new cultivar 'PPP PIZ R05' are similar to plants of the female parent, which is also the most similar commercial variety, 'GEDI TWO CAM' in most horticultural characteristics, however plants of the new cultivar 'PPP PIZ R05' are taller and wider. Also, 'PPP PIZ R05' has more inflorescences per lateral branch. Additionally, the new variety 'PPP PIZ R05' has spoon shape florets. Finally, 'PPP PIZ R05' has a longer inflorescence longevity and the ray florets are a bronze red compared to the dark red ray florets of the female parent and commercial variety 'GEDI TWO CAM'.

Plants of the new cultivar 'PPP PIZ R05' are similar to plants of the male parent 'GEDI ONE SAV' in most horticultural characteristics, however, plants of the new cultivar 'PPP PIZ R05' are taller and wider. Also, the new cultivar has more inflorescences per lateral branch than the male parent. Finally, the male parent has more ray florets per inflorescence and darker red ray florets than the new cultivar 'PPP PIZ R05.'

BRIEF DESCRIPTION OF THE PHOTOGRAPH

The accompanying photograph in FIG. 1 illustrates in full color a typical plant of 'PPP PIZ R05' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP PIZ R05' plants grown in Oxnard, Ventura County, Calif., during the months of May through September 2005. The growing temperature ranged from 12° C. to 15° C. at night to 21° C. to 20° C. during the day. Measurements and numerical values represent averages of typical flowering types.

Botanical classification: *Chrysanthemum morifolium* cultivar 'PPP PIZ R05.'

Commercial classification: Garden-type *Chrysanthemum.*

PROPAGATION

Time to rooting: 7 to 14 days at approximately 21° C.
Root description: Fine, fibrous.

PLANT

Growth habit: Mounding herbaceous perennial.
Height: Approximately 27 cm.
Plant spread: Approximately 50 cm.
Growth rate: Moderate.
Branching characteristics: Free Branching.
Length of lateral branches: Approximately 22 cm.
Number of leaves per lateral branch: Approximately 21.
Age of plant described: Approximately 120 days.

FOLIAGE

Leaf:
*Arrangement.*—Alternate single.
*Average length.*—Approximately 2.5 cm.
*Average width.*—Approximately 2.1 cm.
*Shape of blade.*—Ovate.
*Apex.*—Acuminate.
*Base.*—Attenuate.
*Attachment.*—Stalked.
*Margin.*—Serrate.
*Texture of top surface.*—Lightly pubescent.
*Texture of bottom surface.*—Lightly pubescent.
*Leaf internode length.*—Approximately 1.2 cm.
*Color.*—Young foliage upper side: Near Green 137A. Young foliage under side: Near Green 137D. Mature foliage upper side: Near Green 137A. Mature foliage under side: Near Green 137D.
*Venation.*—Type: Palmately net. Venation color upper side: Near Green 137A. Venation color under side: Near Green 137D.

Petiole:
*Average length.*—Approximately 1.1 cm.
*Color.*—Near Green 137A.
*Diameter.*—Approximately 0.1 cm.

BLOOM

Inflorescence:
*Flowering habit.*—Induced by darkness period greater than 13.5 hours, approximately 49 days of appropriate day length required to induce and develop blooms.
*Inflorescence form.*—Decorative.
*Natural flowering season.*—Approximately first week in September.
*Number of inflorescences per lateral branch.*—Approximately 34.
*Inflorescence diameter.*—Approximately 4.5 cm.
*Inflorescence depth.*—Approximately 1.9 cm.
*Inflorescence longevity on plant.*—Approximately 28 to 32 days.
*Persistence.*—Persistent.

Ray florets:
*Appearance.*—Matte.
*Texture.*—Smooth.
*Average number of ray florets per inflorescence.*—156.
*Shape.*—Spoon.
*Aspect.*—Flat.
*Margin.*—Entire.
*Apex.*—Obtuse.
*Base.*—Fused along 50% of length.
*Length.*—Approximately 1.8 cm.
*Width.*—Approximately 0.5 cm.
*Color.*—Upper surface at first opening: Near Greyed-Red 178A. Upper surface at maturity: Near Greyed-Red 180A. Upper surface at fading: Near Greyed-Red 185A. Under surface at first opening: Near Greyed-Red 181D. Under surface at maturity: Near Greyed-Red 182B. Under surface at fading: Near Greyed-Red 182C.

Disc florets:
*Appearance.*—Shiny.
*Texture.*—Smooth.
*Average number of florets per disc.*—Approximately 7.
*Shape.*—Cylindric.
*Apex.*—Obtuse.
*Average length.*—Approximately 0.3 cm.
*Average width.*—Approximately 0.1 cm.
*Color.*—At first opening: Near Yellow-Green 154B. At maturity: Near Yellow 13A. At fading: Near Yellow 11B.

Peduncle:
*Length.*—At terminal end (shortest): Approximately 6 cm. At lateral end (longest): Approximately 8.2 cm.
*Angle to stem.*—Acute.
*Strength.*—Moderate.
*Color.*—Near Green 137C.
*Habit.*—Upright.
*Diameter.*—Approximately 0.1 cm.
*Surface texture.*—Lightly pubescent.

Inflorescence bud:
*Length.*—Approximately 0.2 cm.
*Diameter.*—Approximately 0.4 cm.
*Form.*—Globular.
*Color.*—Near Green 137D.

Involucral bracts (phyllaries):
*Appearance.*—Matte.
*Texture.*—Lightly pubescent.
*Number.*—Approximately 30.
*Shape.*—Ovate.
*Margin.*—Entire.
*Apex.*—Acute.
*Length.*—Approximately 0.4 cm.
*Width.*—Approximately 0.1 cm.
*Color.*—Upper side: Near Green 137D. Under side: Near Green 137D.

REPRODUCTIVE ORGANS

Ray florets:
*Number of pistils per floret.*—1.
*Stigma shape.*—2 branched.
*Stigma color.*—Near Yellow 2A.
*Style color.*—Near Yellow-Green 154C.
*Style length.*—Approximately 0.4 cm.
*Stamens.*—Absent.

Disc florets:
*Number of pistils per floret.*—1.
*Stigma shape.*—Cylindric.
*Stigma color.*—Near Yellow 12A.
*Style length.*—Approximately 0.1 cm.
*Style color.*—Near Yellow 12D.
*Number of stamens per floret.*—Approximately 5.
*Anther shape.*—Tubular.
*Anther color.*—Near Yellow 12A.
*Pollen color.*—Near Yellow 12A.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP PIZ R05' as herein illustrated and described.

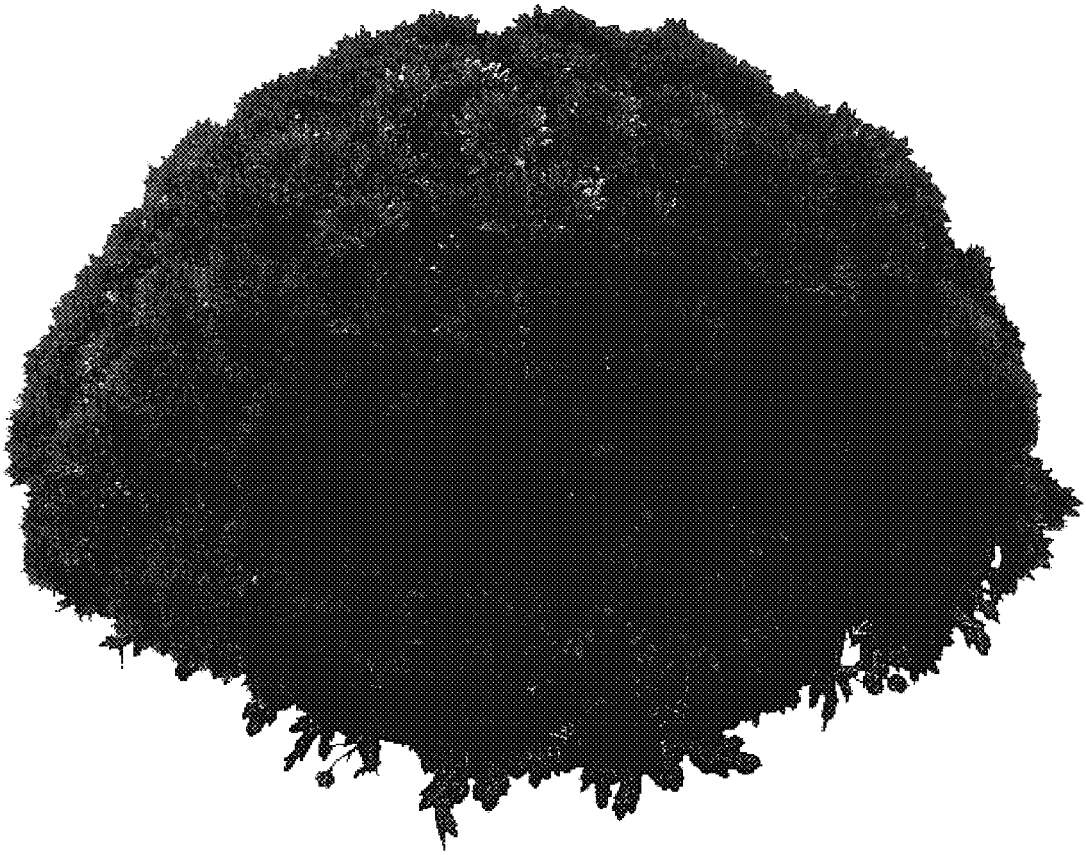

* * * * *